US006151396A

United States Patent [19]

Maier

[11] Patent Number: 6,151,396

[45] Date of Patent: Nov. 21, 2000

[54] ACTIVE ACOUSTIC RESONATOR FOR ABATING NOISE

[75] Inventor: Rudolf Maier, Miesbach, Germany

[73] Assignee: DaimlerChrysler AG, Germany

[21] Appl. No.: 09/042,707

[22] Filed: Mar. 17, 1998

[30] Foreign Application Priority Data

Mar. 18, 1997 [DE] Germany ............................ 197 11 320
Mar. 18, 1997 [EP] European Pat. Off. .............. 97104553

[51] Int. Cl.[7] ........................... A61F 11/06; G10K 11/16; H03B 29/00

[52] U.S. Cl. ........................................ 381/71.14; 381/71.8

[58] Field of Search ................................. 381/71.1, 71.2, 381/71.7, 71.8, 71.14

[56] References Cited

U.S. PATENT DOCUMENTS 5,953,428 9/1999 Silverberg .............................. 381/71.8

FOREIGN PATENT DOCUMENTS 0 434 468 A2 6/1991 European Pat. Off. .
28 14 093 C2 8/1979 Germany .
38 21 939 A1 1/1989 Germany .

*Primary Examiner*—Minsun Oh Harvey
*Attorney, Agent, or Firm*—McGlew and Tuttle, P.C.

[57] ABSTRACT

An active acoustic resonator is provided for noise reduction, with a sound generator having a membrane, with a sensor for measuring the membrane motion, with an actuator for driving the membrane, as well as with a controller receiving the measured signal of the sensor and generating control signals for the actuator. A transfer function ($F_R$) of the controller is proportional to a quotient, whose numerator ($F_{BP}$) has the transfer behavior of a band pass filter with variable center frequency ($f_0$), and whose denominator represents the transfer function ($F_U$) of the actuator.

4 Claims, 2 Drawing Sheets

Fig.3
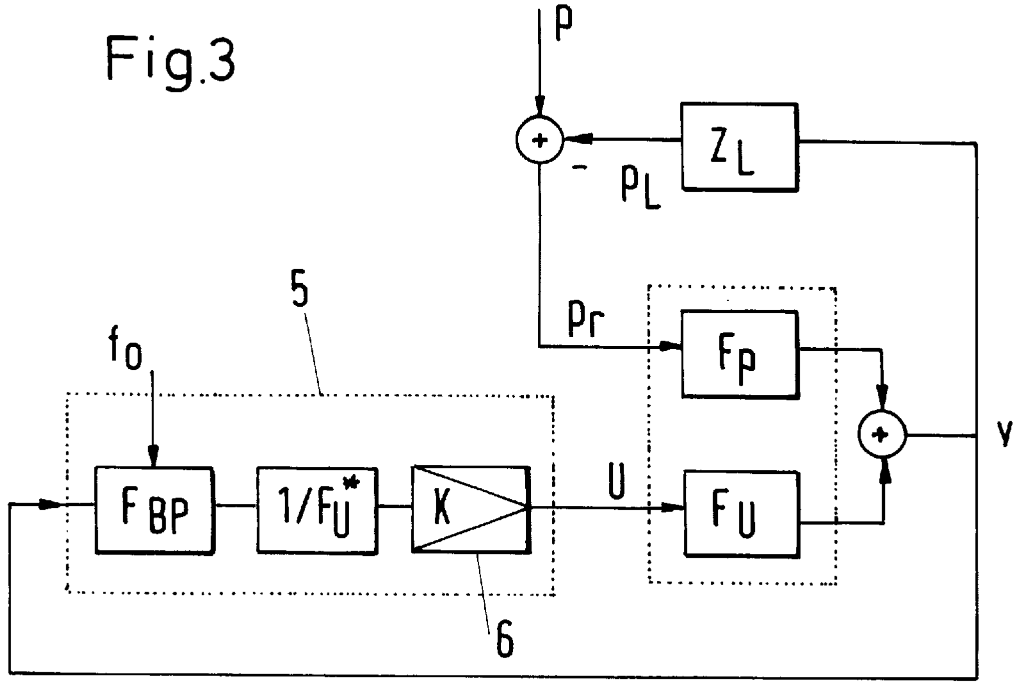
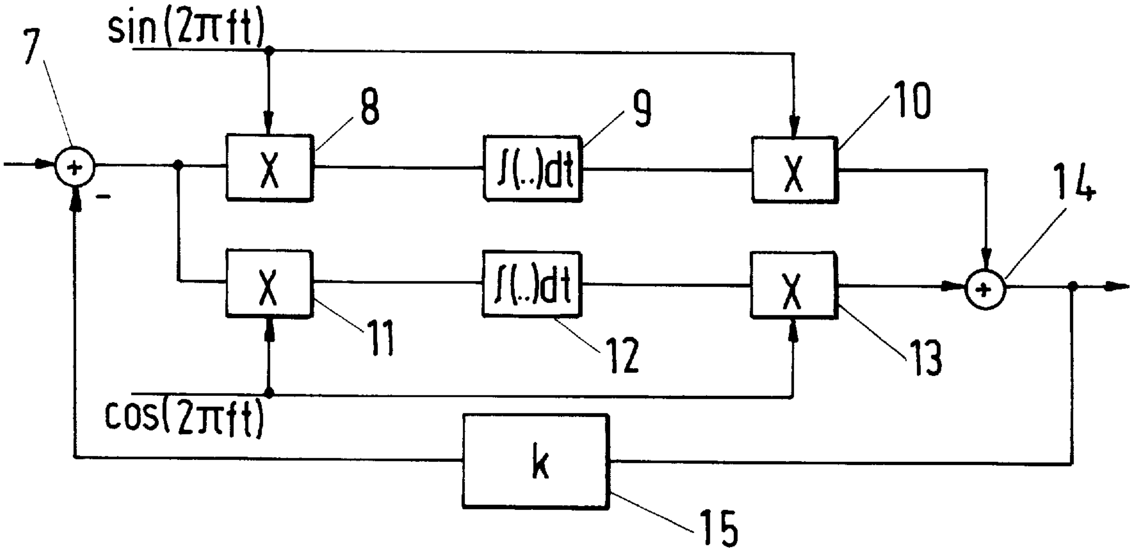
Fig.4

ACTIVE ACOUSTIC RESONATOR FOR ABATING NOISE

The present invention pertains to an active acoustic resonator for noise reduction according to the preamble of patent claim 1.

Such an acoustic resonator or sound absorber has been known from DE-PS 28 14 093. The acoustic resonator described there comprises essentially a sound generator having a membrane, a sensor for measuring the motion of the membrane, an actuator for driving the membrane, as well as a controller receiving the measured signal of the sensor and generating control signals for the actuator.

One principal drawback of this prior-art acoustic resonator is that a simple setting or automatic tracking of the working frequency with respect to an at least approximately known interfering frequency is not possible there. The object of the present invention is to eliminate this drawback.

This object is accomplished according to the present invention by the features contained in the characterizing part of patent claim 1. Additional embodiments of the present invention are described in patent claims 2 and 3.

Quite generally, acoustic resonators can be used in various ways for absorbing and damping sound. Passive resonators require, especially in the case of low-frequency applications, a very large overall volume. Furthermore, all parameters are set by the design. In contrast, the concept of the active resonator permits a simple adaptation of all essential parameters without any design changes and it also makes possible their adaptation to the particular operating conditions even during the operation. Contrary to other arrangements for active noise reduction, the active resonator is characterized by a simple design, because microphone is needed.

Figure 1:
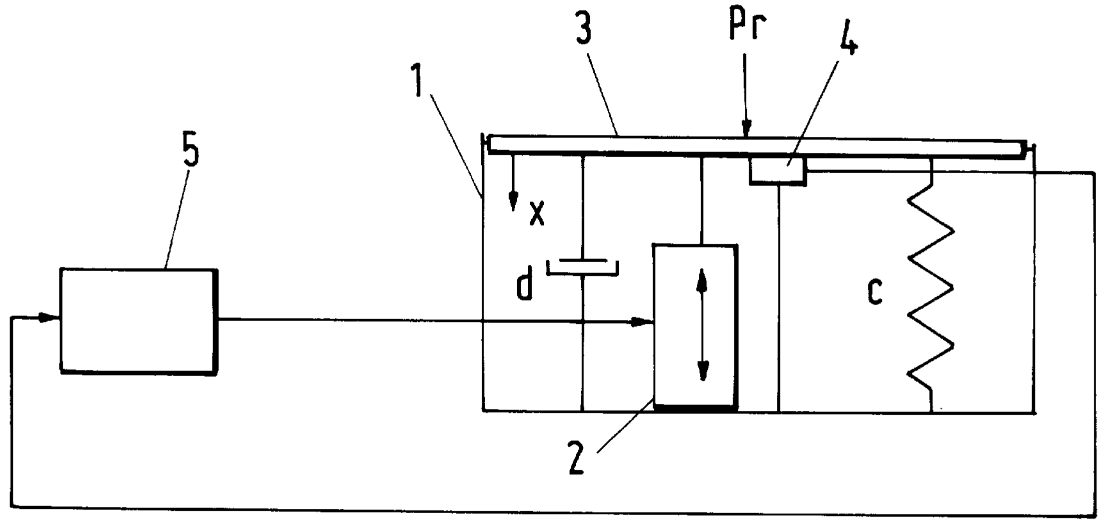

The general design of an active resonator is shown in FIG. 1. A housing 1 is closed to the outside by a membrane 3, which is able to vibrate. This may be set into motion by an actuator, and a sensor 4 is provided for measuring the motion of the membrane (velocity or acceleration). Furthermore, an electronic control device, namely, a controller 5, which receives the measured signal of the sensor 4 as an input signal, is present. By means of its output signal, this controller 5 controls the actuator 2, which forms a sound generator together with the membrane 3. Depending on the principle of measurement of the sensor 4, the membrane deflection x, the membrane velocity x, or the membrane acceleration x may be used as the input signal for the controller 5. A damping factor d as well as a spring rate c are also indicated as additional parameters of the membrane vibration in FIG. 1.

Figure 2:
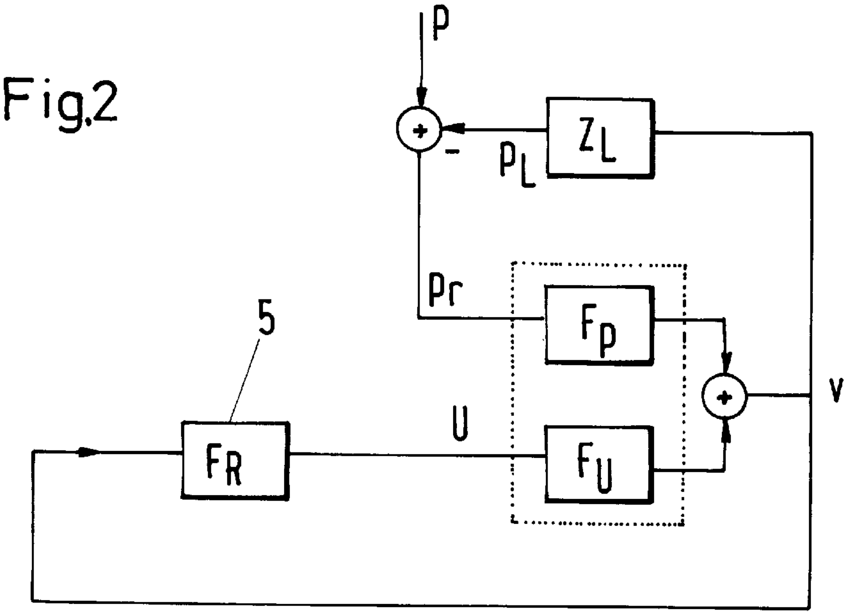

A control engineering block diagram of this active resonator is shown in FIG. 2. The individual blocks are characterized by transfer functions, i.e., the transfer behavior in the frequency range. The sound generator can be described by two transfer functions, which reflect the transfer behavior between the membrane motion and the sound pressure acting on the membrane, on the one hand, and that between the membrane motion and the exciting signal for the actuator part, namely, the control voltage U, on the other hand. The first transfer function $F_p$ consequently transfers the resulting sound pressure $p_r$ into a first component of the membrane motion. The second transfer function $F_U$ transforms the control voltage U into a second component of the membrane motion. The two components add up to the resulting membrane velocity v. The measured signal corresponding to this velocity is sent to the controller 5, whose transfer function is determined by $F_R$. This in turn generates control voltage U as the output signal. Via the ambient air, the membrane velocity v brings about a pressure component $p_L$, which counteracts the sound pressure p acting from the outside, from which the pressure $p_r$ acting directly on the membrane is finally obtained. The relationship between the membrane velocity v and the pressure component $p_L$ brought about by this is represented by the impedance $Z_L$ of the air.

The impedance Z of the active resonator is determined by the transfer function between the resulting sound pressure $p_r$ and the membrane velocity v according to the following equation (1):

$$Z = \frac{p_r}{v} = \frac{1 - F_U F_R}{F_p} \quad (1)$$

The relationship corresponding to the right-hand side of the equation can be read directly from FIG. 2. The sound pressure reduction $p_r/p$ is thus found to be:

$$\frac{p_r}{p} = \frac{1 - F_U F_R}{1 + F_p Z_L - F_U F_R} = \frac{Z}{Z_L + Z} \quad (2)$$

This equation shows that the impedance Z of the active resonator should possibly be lower than the impedance $Z_L$ of the air in order to achieve appreciable sound pressure reductions. If Z and $Z_L$ are equal, the sound pressure is reduced by 6 dB, and a maximum absorption is reached.

The following expression follows from Equation (1) for the transfer function $F_R$, which generates a desired impedance Z:

$$F_R = \frac{1}{F_U}(1 - F_p Z) \quad (3)$$

Since the impedance Z of the active resonator depends on the impedance $Z_L$ of the air, the transfer function $F_R$ of the controller 5 is completely defined by the properties of the sound generator ($F_p$, $F_U$) and the desired impedance Z.

The present invention is based on the idea of providing the active resonator with an adjustable resonance frequency. To do so, the desired impedance Z must have a minimum at a certain, desired frequency $f_0$. Consequently, the following form can be selected for Z:

$$Z = \frac{F_N}{F_p} \quad (4)$$

in which $F_N$ is defined with the Laplace variable s by the following expression:

$$F_N = \frac{s^2 + d_z s + (2\pi f_0)^2}{s^2 + d_N s + (2\pi f_0)^2} \quad (5)$$

If the value of $d_z$ is selected to be very small compared with $d_N$, $F_N$ has, as desired, a minimum at the resonance frequency $f_0$. The transfer function of the controller 5 now assumes the following form:

$$F_R = \frac{1}{F_U}\left(1 - F_N \equiv \frac{F_{BP}}{F_U}\right. \quad (6)$$

The transfer function $F_R$ of the controller 5 is consequently equal or at least proportional according to the present invention to a quotient, whose numerator $F_{BP}$ has the transfer behavior of a band pass filter with variable center frequency $f_0$, and whose denominator is defined by the transfer function $F_U$ of the actuator 2.

The present invention will be explained in greater detail below on the basis of figures. In the drawings, FIG. 1 shows the general design of an active resonator, FIG. 2 shows a corresponding block diagram, FIG. 3 shows the block diagram of an active acoustic resonator according to the present invention, and FIG. 4 shows the block diagram of a band pass filter used in the controller according to the present invention.

With the exception of the controller 5, FIG. 3 corresponds to the block diagram according to FIG. 2. The transfer function $F_R$ of the controller 5 assumes the form shown on the right-hand side of Equation (6) here. A proportionality factor K, embodied by an amplifier 6, is also added there, so that the transfer function $F_R$ of the controller 5 can be described as follows:

$$F_R = \frac{K}{F_U^*} F_{BP},\ 0 < K \leq \tag{7}$$

$F_{BP}$ represents a band pass filter with the center frequency $f_0$ here, wherein $F_{BP}$ $(j2\pi f_0)=1$. The quotient $/F_U^*$ represents an approximation of $1/F_U$. By introducing Equation (7) into Equation (3), the following expression is thus obtained as the impedance $Z^*$ of the active acoustic resonator:

$$Z^* = \frac{1 - KF_{BP}}{F_p} \tag{8}$$

The impedance $Z^*$ of the active acoustic resonator according to the present invention is thus reduced most strongly at the working frequency $f_0$, namely, to the value $(K-1)/F_p$ $(j2\pi f_0)$. The value 0 is obtained for the impedance $Z^*$ as the extreme case for K=1 at the working frequency $f_0$.

The exact embodiment of the inverse transfer behavior of $F_U$ is, in general, impossible. However, it is always possible for typical sound converters, such as electrodynamic and electrostatic loudspeakers, to form a filter function that can be embodied for a certain frequency range, which closely approximates $1/F_U$. It is especially important in this connection for the phase error of the approximation to be as low as possible. It is advantageous to design the sound converter such that its resonance frequency is located in the range of the desired working frequency.

Thus, an active acoustic resonator, whose working frequency is tracked to an interfering frequency in a simple manner, is obtained by the use of a band pass filter, in which the center frequency is tracked to a preset desired frequency.

It should be possible for practical applications to be able to directly set the resonance frequency of the active acoustic resonator within certain limits. This can be accomplished by the center frequency $f_0$ of the above-mentioned band pass filter being influenced by an external signal. This is indicated by an arrow entering the block for $F_{BP}$ from the top in FIG. 3. Furthermore, the impedance of the active acoustic resonator can be influenced by means of the gain of the controller or by means of the proportionality factor K, as is apparent from Equation (8).

FIG. 4 shows a possibility of how the adjustability of the center frequency $f_0$ can be accomplished. The circuit shown is a band pass filter, at the input of which shown on the left in FIG. 3 the velocity signal v is present, and whose output shown to the right provides a signal, to which the transfer function $1/F_U^*$ as well as the gain factor K are to be superimposed. The input signal first enters an adding member 7, in which a feedback signal, which corresponds to the output signal to which the gain factor k is superimposed, is subtracted. The sum signal thus formed subsequently passes through two parallel forward branches, in which a first multiplication member 8, 11, an integrator 9, 12, as well as a second multiplication member 10, 13 are arranged downstream of one another. The outputs of these two forward branches converge in another adding member 14, in which an output signal is finally formed. As was mentioned above, the gain factor k is superimposed to this [output signal] in an amplification member 15 and is fed back to the input, i.e., the adding member 7. A sinus function that is variable over time at the frequency $f=f_0$ is applied in the multiplication members 8, 11 of the first forward branch, and a corresponding cosine function is applied in the multiplication members 11, 13 of the second forward branch. A band pass filter, in which the center frequency $f_0$ can be specifically changed by an intervention from the outside, is thus embodied. The bandwidth of the band pass filter can be set with the gain factor k. The bandwidth of th active acoustic resonator a function of the bandwidth of the band pass filter. A possible amplitude error in the approximation of $1/F_U$, which is accepted, e.g., in favor of a small phase error, can be compensated in a controlled manner with band pass filter according to FIG. 4 by a frequency-dependent gain, i.e., $K=K(f_0)$.

The entire controller may be designed with analog or digital hardware or with mixed analog-digital hardware.

What is claimed is:

1. An active acoustic resonator for noise reduction, comprising:

a sound generator having a membrane;

a sensor for measuring membrane motion;

an actuator for driving the membrane;

a controller receiving the measured signal of the sensor and generating control signals for the actuator, said controller having a transfer function $(F_R)$ which is proportional to a quotient, whose numerator $(F_{BP})$ has the transfer behavior of a band pass filter with variable center frequency $(f_0)$, and whose denominator represents the transfer function $(F_U)$ of the actuator.

2. The resonator in accordance with claim 1, wherein a circuit embodying the band pass filter has, between its input and its output, two mutually parallel forward branches each with an integrator arranged between two multipliers as well as a return branch that contains an amplification member and feeds the output back to the input, wherein a sinus signal is applied to said multipliers in one forward branch and a cosine signal with the center frequency $(f_0)$ of the band pass filter is applied to said multipliers of the other branch.

3. Resonator in accordance with claim 1, wherein a proportionality factor (K) of the transfer function $(F_R)$ of said controller is variable as a function of center frequency $(f_0)$.

4. An active acoustic resonator for noise reduction, comprising:

a sound generator having a membrane;

a sensor for measuring membrane motion;

an actuator for driving the membrane;

a controller receiving the measured signal of the sensor and generating control signals for the actuator, said controller having a transfer function ($F_R$) which is proportional to a quotient, whose numerator ($F_{BP}$) has the transfer behavior of a band pass filter with variable center frequency ($f_0$), and whose denominator represents the transfer function ($F_U$) of the actuator;

a circuit embodying the band pass filter has, between its input and its output, two mutually parallel forward branches each with an integrator arranged between two multipliers as well as a return branch that contains an amplification member and feeds the output back to the input, wherein a sinus signal is applied to said multipliers in one forward branch and a cosine signal with the center frequency ($f_0$) of the band pass filter is applied to said multipliers of the other branch.

* * * * *